United States Patent [19]

Ueda et al.

[11] Patent Number: 5,055,404

[45] Date of Patent: Oct. 8, 1991

[54] MONOCLONAL ANTIBODY SPECIFICALLY REACTIVE TO SURFACE OF HUMAN PROSTATIC EPITHELIAL CELLS

[76] Inventors: Masamichi Ueda, 13-4, Toyosato 6-chome, Higashiyodogawa-ku, Osaka-shi, Osaka; Tatsuhiro Yoshiki, 1-23, Takanohigashihiraki-cho, Sakyo-ku, Kyoto-shi, Kyoto, both of Japan

[21] Appl. No.: 390,985

[22] Filed: Aug. 7, 1989

[30] Foreign Application Priority Data

Aug. 9, 1988 [JP] Japan ................... 63-200866

[51] Int. Cl.$^5$ .............. C12N 5/20; C12N 15/02; C07K 15/28; C12P 21/08
[52] U.S. Cl. .................. 435/240.27; 530/387; 435/70.21; 435/172.2
[58] Field of Search ............ 530/387; 435/240.27, 435/172.2, 70.21

[56] References Cited

U.S. PATENT DOCUMENTS 4,446,122  5/1985  Chu et al. ................ 424/1.1

FOREIGN PATENT DOCUMENTS 2139645  11/1984  United Kingdom .

OTHER PUBLICATIONS

Wright et al., Cancer Res., 43:5509–16, 1983.
Ware et al., Cancer Res. 42: 1215–22, 1982.
Campbell, "Monoclonal Antibody Technology" Elsevier, 1984, 265 p.
Frankel; PNAS 79: 903–907, 1982.
Webb; Cancer Immunol. Immunother 17: 17—17, 1984.
Finstad; PNAS 82: 2955–59, 1985.
Brawer; Cancer Res. 45: 3663–67, 1985.

*Primary Examiner*—Esther L. Kepplinger
*Assistant Examiner*—Paula Hutzell

[57] ABSTRACT

Monoclonal antibodies Pes-1, Pes-2, Pes-3 and Pes-4 which are respectively produced by hybridomas hPro-1.10G (FERM BP-1986), hPro-4.10H (FERM BP-2634), hPro-5.10F and hPro-1.5F specifically bind to the surface of human prostatic epithelial cells. They do not bind to any of many other normal or tumor tissues. The monoclonal antibodies are prepared by immunizing an animal with pieces of epithelial tissue from human prostate as an antigen, fusing antibody-producing cells of the animal with myeloma cells, selecting a hybridoma which produces the antibody, cultivating the hybridoma and recovering the antibody. The monoclonal antibodies have utility for histological examination for metastatic nests in prostatic cancer, preoperative examination in prostatic cancer, diagnosis of prostatic cancer.

4 Claims, 1 Drawing Sheet

MONOCLONAL ANTIBODY SPECIFICALLY REACTIVE TO SURFACE OF HUMAN PROSTATIC EPITHELIAL CELLS

The present invention relates to a novel monoclonal antibody specifically reactive to the surface of human prostatic epithelial cells, a hybridoma producing said monoclonal antibody, and a method for preparing said monoclonal antibody.

With recent development of a method for preparing monoclonal antibodies, which are specifically reactive to a known or unknown antigen, by a cell fusion of antibody-producing cells of an animal immunized with said antigen and myeloma cells, there have been prepared a number of monoclonal antibodies to various antigens which are very useful in clinical and experimental fields. For example, a monoclonal antibody highly specific to a tumor-associated antigen will be useful for diagnosis of the tumor, for determination of the existing region of the tumor, and for therapy of the tumor. Accordingly, many attempts to prepare a monoclonal antibody specifically reactive to a tumor-associated antigen have been made for a variety of tumors. However, previously prepared antibodies often react also with normal cells in various organs, or they do not necessarily react in common with tumors in many patients. With respect to the prostatic cancer with which the present invention is concerned, any monoclonal antibody which is specifically reactive to the tumor-associated antigen and can be used in common for many patients has not yet been obtained.

BRIEF DESCRIPTION OF THE INVENTION

Under such circumstances, the present inventors have intensively studied to construct a monoclonal antibody commonly recognizing human prostatic epithelial tissues without regard to tumor-associated antigens thereof, and have obtained a monoclonal antibody recognizing "differentiated antigen" specifically existing on any epithelial cell of human prostate, which antibody reacts with cells from normal prostate, cells from benign prostatic hyperplasia (BPH), and any cell from prostatic cancer.

An object of the present invention is to provide a monoclonal antibody specifically reactive to the surface antigen on epithelial cells of human prostate. Another object of the invention is to provide a hybridoma producing the monoclonal antibody. A further object of the invention is to provide a method for preparing the hybridoma and monoclonal antibody. These objects and advantages of the invention will be apparent from the following description.

DETAILED DESCRIPTION OF THE INVENTION

Figure 1:
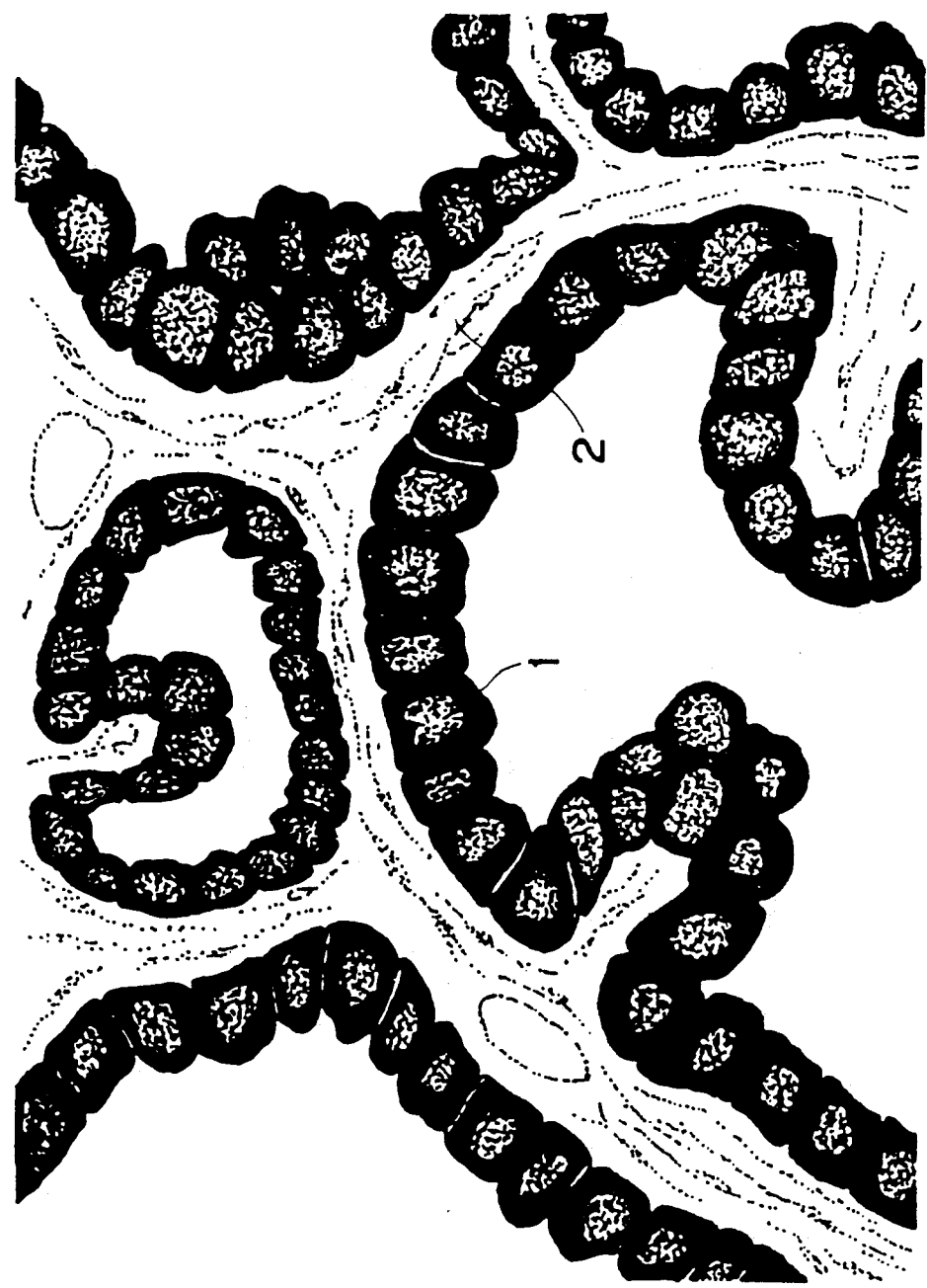
FIG. 1 shows immunofluorescent staining of BPH tissue with FITC-conjugated rabbit immunoglobulins to mouse immunoglobulins.

The monoclonal antibody and the hybridoma according to the present invention can be prepared as follows:
i) obtaining epithelial tissue chips from human prostate, for example, from prostate delivered from patients of BPH or prostatic cancer, and immunizing an animal with the chips as an antigen;
ii) fusing antibody-producing cells from said immunized animal with myeloma cells, and selecting hybridomas capable of producing a monoclonal antibody specifically reactive to the surface antigen on the human prostate epithelial cells; and
iii) cultivating said hybridomas under a suitable condition, and recovering said monoclonal antibody.

The immunization of the animal of the step i) can be conducted by administering as an antigen epithelial tissue chips separated from prostate gland to an animal and further treating the animal with the same antigen at the appropriate intervals. The epithelial tissue chips are usually administered to the animal in the form of a suspension in physiological saline. Alternatively, without separating the epithelial tissue chips, the whole prostate gland may be cut into small pieces and suspended in physiological saline to use as the antigen.

Species of the animal to be immunized may be mouse, rat, or the like, and the preferred one is BALB/c mouse.

The cell fusion of the step ii) can be usually carried out using the antibody-producing cells of the animal immunized in the step i) and myeloma cells.

The most preferred antibody-producing cells are spleen cells of the above BALB/c mouse, while other cells, for example, mouse lymph node cells, peripheral lymphocytes, and rat lymphocytes may also be used.

The preferred myeloma cells are mouse myeloma cell line X63-Ag8.653, while other cell lines such as X63-Ag8, NS1-Ag4/1, MPC-11, and 210.RCY3 may also be used.

The cell fusion procedures include polyethylene glycol, HVJ, and electroporation procedures.

The selection of the resulting hybridomas can be performed, for example, by cultivating the hybridomas in a suitable medium, reacting the cultured medium with human prostate gland and other organ such as kidney, treating with anti-mouse IgG rabbit immunoglobulin labeled with fluorescein isothiocyanate (FITC), etc., observing the resultant with a fluorescence microscope or any other conventional means, and selecting the hybridomas capable of producing the desired monoclonal antibody which reacts with epithelial tissue of prostate gland but neither with stroma of prostate gland, nor with other organs such as kidney. Subsequently, the selected hybridomas are cloned by the limiting dilution method.

The recovery of the monoclonal antibody of the step iii) can be carried out by a conventional method, for example, by injecting the hybridomas obtained in the step ii) into the peritoneal cavity of a mouse and then isolating the antibody from the ascites of the mouse thus treated. The antibody may also be recovered from a culture medium of the hybridoma clones using a large-scale culture apparatus in a usual manner. The antibody recovered may be purified by a conventional purification method, such as ammonium sulfate precipitation, molecular sieve chromatography, ion-exchange chromatography, affinity chromatography, or the like.

The monoclonal antibodies of the present invention recognize "differentiated antigen" specifically existing on any epithelial cells of human prostate gland, as shown in Example below. The present monoclonal antibodies react with the surface antigen on the epithelial cells from normal prostate, benign prostatic hyperplasia, and prostatic cancer. The present antibodies, based on the above characteristics, have the following utilities.

(1) Histological examination of metastatic nests in prostatic cancer

In patients having prostatic cancer, metastasis of tumor cells to lymph nodes and then to bone is often found. Accordingly, in the extirpation of the prostatic cancer, the extirpating operation is often applied to the prostate and the lymph nodes to which the tumor cells may metastasize. The monoclonal antibody of the present invention is useful for a rapid examination of the prostatic cancer metastasis before or during the operation for extirpation of the lymph nodes. Furthermore, a postoperative examination with the antibody of the present invention enables to determine a strategy of post-treatment of the patients. These examintions have been successfully conducted as shown in Example below.

(2) Preoperative examination in prostatic cancer

When a monoclonal antibody labeled with an isotope such as 99mTc, $^{131}$I, $^{111}$In is administered to a patient who is diagnosed to have prostatic cancer, it will be observed that the labeled antibody is accumulated on epithelial cells of prostate and tumor cells derived therefrom. If metastatic nests exist, the region thereof can be detected by subsequent scintigraphy. Consequently, operable lesions can be distinguished from inoperable ones, and in the former case, the most appropriate operation can be applied to the patients.

(3) Diagnosis of prostatic cancer

It is expected that an abnormal proliferation of epithelial cells of prostate gland leads to a release of an antigen recognizable by the present antibody into blood, and that the level of the antigen in blood is high in the patient with prostatic cancer. Accordingly, diagnosis of the presence or absence of prostatic cancer can be carried out by detecting the antigen in blood or serum with the present antibody labeled with fluorescent reagents, enzymes, or radioisotopes.

(4) Postoperative treatment

It is believed that the administration of the monoclonal antibody conjugated with a cytotoxin such as carcinostatics can cause metastatic nests to disappear if they are small. Therefore, a cure of disease or a prolonged life can be obtained in patients who have undergone an operation extirpating their primary foci and more than moderate size of metastasized foci, by administering the present antibody conjugated with a suitable cytotoxin to said patient.

The present invention is illustrated by the following Example, but should not be construed to be limited thereto.

EXAMPLE

A. Immunization of Mice

About 1 g of the human prostate tissue from BPH was cut into small pieces, and the tissue chips were stirred up by pipetting in Eagle's minimal essential medium. Standing the medium at room temperature, epithelial cells remained suspended, while stroma was precipitated within a few minutes. The epithelial cells in the supernatant were collected by centrifugation, and some of them were used for the first immunization. The other part of the cells were suspended in 10% DMSO and 90% fetal bovine serum, and stored frozen in liquid nitrogen for the later immunizations. Seven-week-old BALB/c mice were immunized intraperitoneally 3 times every 3 weeks with $1 \times 10^7$ cells in 1 ml of phosphate-buffered saline (PBS). Three days after the last immunization, the mice were sacrificed and spleen cells were removed.

B. Cell Fusion

The spleen cells obtained in the above step A were fused with mouse myeloma cells (X63-Ag8.653) in a 50% solution of polyethylene glycol 1500 (BDH) at 37° C. The resulting fused cells were plated in 0.1 ml aliquots on 96 well microplate (Corning), and cultivated for 14 days in HAT medium [prepared from RPMI 1640 medium (Nissui) supplemented with 15% fetal bovine serum (Filtron)] with irradiated thymocytes from BALB/c mice. Monoclonal antibodies (MABs) in necessary amounts were secreted into the medium in about two weeks.

C. Screening of Antibodies

Supernatants from actively growing hybridomas were screened by indirect immunofluorescent staining of frozen sections as described below.

The human prostate tissue from BPH and human normal kidney tissue were embedded in the OCT compound (Miles Laboratories, Naperville, Ill.) without fixation, and frozen in liquid nitrogen. About 6 to 8 μm thick of cryostat sections were prepared using low temperature microtome (Reichert) and mounted on neoprene-coated glass slides and air-dried. The sections were overlaid with 0.1 ml of the culture supernatant in the 96 well microplate for 30 min at room temperature. These sections were washed with saline and then treated for 30 min with the fluorescein isothiocyanate (FITC)-conjugated rabbit immunoglobulins to mouse immunoglobulins (DAKOPATTS, Denmark). After washing these sections, sites in the tissues reacted with antibodies in the supernatant were observed under an epifluorescence microscope (Nikon, Tokyo, Japan). Subsequently, wells containing an antibody which reacts with epithelial cells in the prostate tissue but reacts neither with stroma in the prostate tissue nor with the kidney tissue at all were selected.

D. Cloning of Hybridomas

Hybridomas in the wells selected in the above step C were doubly cloned by the limiting dilution method. As a result, four distinct clones producing antibodies which have highly specific reactivity to prostate epithelial cells were obtained.

The above clones designated as hPro-1.10G, hPro-4.10H, hPro-5.10F and hPro-1.5F, which produce monoclonal antibodies Pes-1, 2, 3 and 4, respectively, were deposited in the Fermentation Research Institute, Agency of Industrial Science and Technology 1-3, Higashi 1 chome Tsukuba-shi Ibaraki-ken 305, Japan under accession numbers FERM BP-1986 (under Budapest Treaty), P-10169 which has been transferred to a deposit under Budapest Treaty, P-10170 and P-10168, respectively. The depositing of hPro-1.10G and hPro-1.10H was carried out on Aug. 2, 1988.

To determine the immunoglobulin subclass of the antibodies, the Ouchterlony double-immunodiffusion method with rabbit monospecific antisera to mouse immunoglobulins (Miles, Elkhart, Ind.) was used, and it was found that three antibodies, Pes-1 to 3 belong to IgG$_1$ subclass and one antibody, Pes-4 belongs to IgG$_{2a}$ subclass.

E. Preparation of Large Quantity of Antibody

To obtain a large quantity of antibody, hybridomas cloned in the above step D were injected into the peritoneal cavity of BALB/c mice previously treated with pristane (2,6,10,14-tetramethylpentadecane, Aldrich Chemical Co., Milwaukee, Wis.). IgG was roughly purified from the ascites by 20 to 50% ammonium sulfate precipitation. The material was then applied to affinity chromatography with the protein A agarose (Affi-Gel Protein A, Bio-Rad Laboratories, Richmond, Calif.) which had been washed with 1.5M glycine (pH 8.9) and 3M NaCl buffer, washed with 100 ml of the same buffer, and eluted with 0.1M sodium citrate (pH 6.0 for IgG$_1$, pH4.0 for IgG$_{2a}$). The resulting monoclonal antibodies had high purity of more than 95%, mostly 99%, and were stored at 4° C. in PBS with 10 mM sodium azide.

F. Membrane Location of Antigen Recognized by MAB

The purified monoclonal antibody (MAB) was labeled with labeling reagents to assess the reactivity of living epithelial cells with the antibody. The freshly prepared epithelial cells from BPH were stained with the antibody by the indirect immunofluorescent method as described in the above step C. Almost all the suspended cells were stained well. This indicates that at least some antigens recognized by the present MAB are located on the surface of the plasma membrane. Also, it was found that $^{125}$I-labeled antibody (Iodination beads were employed; NEN) reacted well with the living epithelial cells. These findings confirm that some antigens recognized by MAB are located on the plasma membrane of the prostatic epithelial cells.

G. Specificity of Antibodies i) Reactivity to Prostate:

The MAB from clone 1-10G (Pes-1; IgG$_1$) was found to be strongly reactive to BPH tissue sections. The antibody was reactive to all glandular epithelial cells which could be identified in BPH tissue, and it was not reactive to stromal cells or basal cells at all (FIG. 1). This was the case for all examined BPH tissues (Table 1). The antibody showed the same reactivity to the normal prostate as it did to BPH tissue.

BPH tissue sections fixed with paraformaldehyde or PLP (paraformaldehyde, lysine, sodium periodate) give the same result as those unfixed.

As is seen from FIG. 1 showing immunofluorescent staining of BPH tissue with FITC-conjugated rabbit immunoglobulins to mouse immunoglobulins, wherein the fluoresced surface of the epithelial cells is shown as black, MAB Pes-1 reacted with epithelial cells(1) but did not react with stroma(2).

ii) Reactivity to Various Normal Tissue Other Than Prostate:

MAB failed to react to any normal tissue examined other than the prostate gland (Table 2). MAB did not show any reactivity to various urogenital organs including the seminal vesicle which produces the major part of the semen, or the female urethral glands. It also did not react to the skin, liver, digestive organs or endocrinic organs. Bone, lymph nodes and lung, being the target organs of prostatic cancer metastasis, had no reactivity to MAB.

TABLE 1

Reactivity of monoclonal antibody from clone 1-10G to human prostate

| Tissue type | Positive No./Tested No. |
| --- | --- |
| Normal | 2/2 |
| Hyperplasia | 15/15 |
| Adenocarcinoma | |
| Well-differentiated | 2/2 |
| Moderately differentiated | 4/4 |
| Poorly differentiated | 7/7 |

The apparently normal, hyperplastic or cancerous prostate was embedded in OCT compound without fixation. Each tissue was stained by indirect immunofluorescent staining as described in the step C.

TABLE 2

Reactivity of 4 monoclonal antibodies to various human normal tissues

| Tissue | Positive No./Tested No. |
| --- | --- |
| Urogenital system | |
| Seminal vesicle | 0/2 |
| Spermatic duct | 0/2 |
| Epididymis | 0/2 |
| Testis | 0/2 |
| Sperm | 0/2 |
| Kidney | 0/3 |
| Bladder | 0/1 |
| Ovary | 0/2 |
| Uterus | 0/2 |
| Female urethral gland | 0/1 |
| Digestive system | |
| Salivary gland | 0/2 |
| Stomach | 0/1 |
| Liver | 0/1 |
| Pancreas | 0/1 |
| Small intestine | 0/1 |
| Large intestine | 0/1 |
| Respiratory system | |
| Lung | 0/2 |
| Bronchus | 0/1 |
| Endocrinic system | |
| Thyroid gland | 0/1 |
| Adrenal gland | 0/1 |
| Others | |
| Lymph node | 0/2 |
| Bone | 0/2 |
| Bone marrow | 0/2 |
| Erytheocyte | 0/5 |
| Skin | 0/1 |
| Mammary gland | 0/1 |
| Eye | 0/1 |

Various normal tissues were embedded in the OCT compound without fixation, and each tissue was treated with monoclonal antibodies from clones 1-10G, 1-5F, 4-10H or 5-10F, and then with the FITC-conjugated second antibody. None of the 4 monoclonal antibodies showed reactivity to any human normal tissue except the prostate.

iii) Reactivity to Cancer Cells:

The reactivity of MAB to prostatic cancer tissues was examined by the ABC method (Table 1). MAB reacted strongly to any well-differentiated prostatic cancer cell from two patients. The antibody also reacted to poorly differentiated prostatic cancer cells from seven patients, but the reactivity was weak or heterogenous compared to the reactivity in the case of the well-differentiated tissues.

In four patients with prostatic cancer, a pathological metastasis to the lymph nodes was observed. Two cases were moderately differentiated cancer, and two cases were poorly differentiated cancer. In all cases, the antibody was found to be reactive to the cells in the lymph nodes identified as the metastatic malignant cells. In one patient with prostatic cancer, lung metastasis was observed after autopsy. This lung looked normal macroscopically, but small nests of prostatic cancer cells were observed by ABC staining with MAB Pes-1. In another patient with prostatic cancer, laminectomy was carried out because paralysis was caused by the metastasis to the vertebral bones. MAB Pes-1 reacted well to this metastatic cancer tissue.

The reactivity of the antibody to the cancer tissues other than the prostate was investigated (Table 3). MAB was found not to react to renal cell cancer, renal pelvic cancer, ureteral cancer, bladder cancer, testicular tumor, gastric cancer, colon cancer or pheochromocytoma. The antibody also did not react to any cell line derived from various cancers (Table 4).

The human cell lines utilized in this study were PC-3, PC93, DU145 and LNCaP as prostate adenocarcinoma cell lines; J82 and T24 as bladder carcinoma cell lines; ACHN, A-704 and NC65 as renal cell carcinoma cell lines; SK-HEP-1 as a hepatoma cell line; and SW1116 as a colorectal carcinoma cell line. These cell lines were grown in a nutrient medium supplemented with the serum additives recommended by the supplier of the cell line.

TABLE 3

| | Lack of reactivity of 4 monoclonal antibodies to tumor tissues | |
|---|---|---|
| Tumor | Tissue type | Reactivity |
| Testicular tumor | Embryonal carcinoma + Teratoma | (−) |
| Bladder tumor | Transitional cell carcinoma | (−) |
| Ureteral tumor | Transitional cell carcinoma | (−) |
| Renal pelvic tumor | Transitional cell carcinoma | (−) |
| Renal cell cancer | Adenocarcinoma | (−) |
| Gastric cancer | Adenocarcinoma | (−) |
| Colon cancer | Adenocarcinoma | (−) |
| Pulmonary cancer | Adenocarcinoma | (−) |
| Pheochromocytoma | | (−) |

One specimen of each tumor tissue was obtained from surgical operation. The materials were stained by indirect immunofluorescence with each of 4 MABs as described in the step C.

TABLE 4

| | Lack of reactivity 4 monoclonal antibodies to cell lines | |
|---|---|---|
| Cell line | Origin | Reactivity |
| Prostatic carcinoma | | |
| DU145 | Brain metastasis | (−) |
| LNCaP | Lymph node metastasis | (−) |
| PC-3 | Bone metastasis | (−) |
| PC93 | Primary | (−) |
| Renal cell cancer | | |
| A-704 | Primary | (−) |
| ACHN | Malignant pleural effusion | (−) |
| NC65 | Primary | (−) |
| Bladder carcinoma | | |
| J82 | Primary | (−) |
| T24 | Primary | (−) |
| Hepatoma | | |
| SK-HEP-1 | Ascites | (−) |

TABLE 4-continued

| | Lack of reactivity 4 monoclonal antibodies to cell lines | |
|---|---|---|
| Cell line | Origin | Reactivity |
| Colorectal carcinoma | | |
| SW1116 | Primary | (−) |

Cells were prepared on the glass slide by the cytocentrifuge. They were stained with each of 4 monoclonal antibodies and the FITC-conjugated second antibody as described in Table 2.

iv) Other MABs with Similar Reactivity:

Reactivity of three other MABs from clones 4-10H (Pes-2; IgG$_1$), 5-10F (Pes-3; IgG$_1$) and 1-5F (Pes-4; IgG$_{2a}$) was very similar to that of 1-10G (Pes-1; IgG$_1$). Each MAB was found to be specifically reactive to the epithelial cells of the prostate from normal or BPH donors. They did not react at all to the various normal tissues other than the prostate as in the case of MAB from clone 1-10G. Each MAB was reactive to the surface of the prostatic epithelia cells as in the case of 1-10G. This was indicated by the indirect immunofluorescent staining of the freshly prepared epithelial cells. The reactivity of these MABs to the prostatic cancer tissues from 13 patients was then examined. These MABs were found to be reactive to the cancer tissues from 11 patients as in the case of 1-10G, but did not react to the tissues from 2 patients.

Finally, the reactivity of 4 MABs to the prostate from several animals was tested (Table 5). MABs from 4-10H and 5-10F were reactive to canine, ape and human prostates, and MAB from 1-5F was reactive to ape and human prostates. MAB from 1-10G was not reactive to other animals except humans. On the positively stained tissue sections, all glandular epithelial cells were intensively stained, and the stroma was not stained at all.

TABLE 5

| | Immunofluorescent staining of the prostate from various animals with 4 monoclonal antibodies | | | |
|---|---|---|---|---|
| | 1-10G | 1-5F | 4-10H | 5-10F |
| BALB/c mouse | − | − | − | − |
| Wister/ST Rat | − | − | − | − |
| Cat | − | − | − | − |
| Dog | − | − | + | + |
| Crab-eating macaque | − | + | + | + |
| Man | + | + | + | + |

The tissue sections of the prostate from various animals were stained with each of 4 monoclonal antibodies and the FITC-conjugated second antibody. The mouse prostate was stained by the direct immunofluorescent method. In the positive cases described here, all epithelial cells were strongly stained, and stromal tissues were not stained at all.

What is claimed is:

1. A monoclonal antibody Pes-1 which is produced by hybridoma hPro-1.10G having the Fermentation Research Institute accession number FERM BP-1986 and specifically binds to the surface of human prostatic epithelial cells.

2. A monoclonal antibody Pes-2 which is produced by hybridoma hPro-4.10H having the Fermentation Research Institute accession number FERM BP-2634 and specifically binds to the surface of human prostatic epithelial cells.

3. A hybridoma hPro-1.10G having the Fermentation Research Institute accession number FERM BP-1986.

4. A hybridoma hPro-4.10H having the Fermentation Research Institute accession number FERM BP-2634.

* * * * *